(12) United States Patent
Di Miro et al.

(10) Patent No.: US 9,377,425 B2
(45) Date of Patent: Jun. 28, 2016

(54) METHOD AND DEVICE FOR REGENERATING A PARTICLE SENSOR

(71) Applicant: Robert Bosch GmbH, Stuttgart (DE)

(72) Inventors: Ariel Di Miro, Stuttgart (DE);
Bernhard Kamp, Ludwigsburg (DE);
Michael Bessen, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 237 days.

(21) Appl. No.: 14/188,185

(22) Filed: Feb. 24, 2014

(65) Prior Publication Data

US 2014/0238108 A1    Aug. 28, 2014

(30) Foreign Application Priority Data

Feb. 22, 2013    (DE) .......................... 10 2013 202 980

(51) Int. Cl.
*G01N 27/04* (2006.01)
*G01N 15/06* (2006.01)
*G01N 15/00* (2006.01)

(52) U.S. Cl.
CPC ................ *G01N 27/04* (2013.01); *G01N 15/06* (2013.01); *G01N 15/0606* (2013.01); *G01N 15/0656* (2013.01); *G01N 2015/0046* (2013.01)

(58) Field of Classification Search
CPC .................................................... G01N 27/04
USPC ....................................................... 73/28.01
See application file for complete search history.

(56) References Cited

U.S. PATENT DOCUMENTS

| 5,321,897 A * | 6/1994 | Holst .................... D06F 58/266 219/690 |
| 5,437,002 A * | 7/1995 | Bennett ............. A47J 27/21091 219/497 |
| 2006/0170015 A1* | 8/2006 | Wienand ............ G01N 27/4075 257/254 |
| 2009/0217737 A1* | 9/2009 | Dorfmueller .......... F01N 11/00 73/28.01 |
| 2014/0156126 A1* | 6/2014 | Tran ................... B60G 17/0165 701/22 |

FOREIGN PATENT DOCUMENTS

DE    10133384    1/2003

* cited by examiner

*Primary Examiner* — Hezron E Williams
*Assistant Examiner* — David Z Huang
(74) *Attorney, Agent, or Firm* — Michael Best & Friedrich LLP

(57) ABSTRACT

A method for regenerating a particle sensor, which comprises a ceramic base body, in the exhaust gas duct of an internal combustion engine for driving a motor vehicle, wherein a particle loading of the particle sensor is determined by applying an electrical voltage between at least two electrodes with interdigital arrangement, a temperature of the particle sensor is determined with a temperature sensor mounted to the ceramic base body or from the electrical resistance of a heating element and said particle sensor is regenerated by means of heating with the electrical heating element.

22 Claims, 2 Drawing Sheets

METHOD AND DEVICE FOR REGENERATING A PARTICLE SENSOR

BACKGROUND OF THE INVENTION

The invention relates to a method for regenerating a particle sensor, which comprises a ceramic base body, in the exhaust gas duct of an internal combustion engine for driving a motor vehicle, wherein a particle load of the particle sensor is determined by applying an electric voltage between at least two electrodes with interdigital arrangement, a temperature of the particle sensor is determined with a temperature sensor or meander mounted to the ceramic base body or from the electrical resistance of a heating element, and the particle sensor is regenerated by heating with the electrical heating element.

The invention further relates to a device for regenerating a particle sensor, which comprises a ceramic base body, in the exhaust gas duct of an internal combustion engine, wherein the particle sensor comprises at least two electrodes with interdigital arrangement for determining a particle load, a temperature sensor or meander mounted to the ceramic base body for determining a sensor temperature of the particle sensor and an electrical heating element for regenerating said particle sensor, and wherein an engine management system is provided for controlling the internal combustion engine and for acquiring and evaluating output signals of the particle sensor.

Legislative regulations stipulate the monitoring of the composition of the exhaust gas of internal combustion engines for compliance to limit values. Particle sensors are, for example, used to monitor particulate emissions of internal combustion engines and for the on-board diagnostics (OBD) within the scope of a functional monitoring of particle filters. In this regard, collecting, resistive particle sensors (particulate matter sensors or PM sensors) are known which evaluate a change in the properties of an interdigital electrode structure on the basis of particle deposits. Two or a plurality of electrodes can be provided which engage in one another in a comb-like manner. Downstream of the diesel particle filter, the exhaust gas of the internal combustion engine is thereby guided past the electrode structure by means of a double-walled protective pipe construction. Due to an increasing number of particles deposited on the particle sensor, the electrodes are bridged by the particles, which results in a decrease in electrical resistance with increasing particle deposit, in a decrease in impedance or in a change in a characteristic variable related to the resistance or the impedance, such as a voltage and/or a current. For evaluation purposes, a threshold value, for example a measurement current between the electrodes, is generally defined and the time up to achieving the threshold value is used as the measurement for the deposited particle quantity. The rate of change of a signal can also alternatively be evaluated during the particle deposition.

The German patent publication DE 101 33 384 A1 discloses a resistive particle sensor. The particle sensor is constructed from two comb-like electrodes which engage in one another and are at least partially covered by a capturing sleeve. If particles are deposited on the particle sensor from a stream of gas, this leads to a change in the impedance of the particle sensor which can be evaluated, and from which the quantity of deposited particles and therefore the quantity of particles carried along in the exhaust gas can be determined.

If the particle sensor is fully loaded, the deposited particles are burned off in a regeneration phase with the aid of a heating element integrated in the particle sensor. To this end, the ceramic base body of the particle sensor is heated up to a high temperature, whereby said base body is however susceptible to damage due to regional thermal shock which can result from adherent or impacting water droplets. A regeneration of the particle sensor can therefore only be initiated if it can be assumed that no water can reach the particle sensor. To this end, a heat quantity calculation is carried out in an engine management system associated with the internal combustion engine, and a dew point release is provided if no water is presumably to be expected. The underlying assumptions are thereby based on a typical maximum quantity of water in the exhaust gas system which typically occurs during cold starting.

Such a consideration does not include a case like driving through water in which the outlet of the exhaust gas system can lie below the water line and water can penetrate into the exhaust gas system or in which the exhaust gas system can be so greatly cooled down from the outside that the dew point of the gas mixture situated therein is undershot. Ingressed or condensed water is in fact expelled again by means of exhaust gases. After a detected water crossing, the point must however be initially reached where conditions again prevail in the exhaust gas system which are required for a normal dew point release via the thereby utilized pipe wall temperature models and heat quantity integrals in the engine management system.

SUMMARY OF THE INVENTION

It is therefore the task of the invention to provide a method which also enables a regeneration of a particle sensor without the risk of damage by temperature shock even, e.g., after a water crossing operation.

It is furthermore the aim of the invention to provide a corresponding device for carrying out the method.

The aim relating to the method is met in that, after the motor vehicle has driven through water with the heating element switched off and the electrodes free of voltage, the temperature of the particle sensor, an exhaust gas temperature and/or a pipe wall temperature are determined as a release condition of the particle sensor for regeneration or for a measurement phase and in that the release condition is considered to be fulfilled if the temperature exceeds a predetermined release temperature. In order to prevent damage to the ceramic base body of the particle sensor due to large regional temperature differences when water strikes the hot particle sensor, the temperature is determined on the unheated particle sensor and compared to the boiling point of water. In the event that the sensor temperature lies above the boiling point temperature in this operating mode, it can be assumed that no water is adhering to the sensor. If the sensor temperature is still below or in the range of the boiling temperature after a water crossing operation of the vehicle in which water can penetrate into the exhaust gas system or in which the exhaust gas system can be externally cooled down so much by the water that the dew point of the gas mixture situated in the exhaust gas system is undershot, an immediate protective heating of the particle sensor can initially be omitted. During protective heating of the particle sensor, the heater is operated at reduced power in order to evaporate traces of water. If large quantities of water are, however, present in the system after a water crossing operation, protective heating is not yet useful. If the interdigital electrodes which determine a particle coating are switched free of voltage in this operating mode, damage to said electrodes by electrolytic processes is prevented.

If the release condition is combined with a dew point release in order to release the particle sensor or if the release condition initiates a dew point release, the protection of the particle sensor from damage can be further improved. A heat quantity calculation is carried out during the dew point release with the aim of ensuring that water can no longer be present at the sensor position under typical operating conditions. This typically includes the water quantity in the system during cold starting, however not water that has ingressed into the exhaust gas system after driving through water.

An improvement in enabling a regeneration or measurement phase of the particle sensor is achieved in that, in order to release the particle sensor, the release condition from the temperature of the particle sensor is combined with a release from the detection of a water crossing by the vehicle.

One embodiment of the method according to the invention provides that a profile of the temperature of the particle sensor, the exhaust gas temperature and/or the pipe wall temperature are acquired after a water crossing operation of the vehicle and that the release condition is considered fulfilled after a detected temperature plateau if the predetermined release temperature has been exceeded. When analyzing the temperature profile it can be suggested from the occurrence of the temperature plateau that water is evaporating in the system in this phase and holds the temperature approximately constant due to the heat quantity thereby absorbed. If an end of the plateau phase is determined, this means that water located in the system has substantially evaporated and that the release procedures that are typically provided for releasing a regeneration or a measurement phase of the particle sensor can be started.

The inventive operation is preferably carried out in a control device in structural proximity to the particle sensor and provision is made for the heating element and the voltage at the electrodes to be switched off after an on-site control device of the particle sensor detects the vehicle is being driven through water and for a switch-off signal to be sent to a higher-level engine management system. This outsourcing of a part of the operation simplifies the system. The temperature analysis is carried out in the higher-level engine control device with the aid of the temperature information transmitted by the particle sensor.

The aim relating to the device is met in that a circuit or a program sequence for detecting a water crossing operation, for evaluating the sensor temperature, an exhaust gas temperature and/or a pipe wall temperature is provided in the engine management system, in that, after a water crossing operation, a release condition of the particle sensor for regeneration or for a measurement phase is fulfilled if the sensor temperature, the exhaust gas temperature and/or the pipe wall temperature exceed a predetermined release temperature. If the release condition is not fulfilled and thus there is possibly water on the particle sensor, a measurement phase is not yet useful because the resistance between the interdigital electrodes can also be caused by water instead of from sooty particles. The aforementioned pipe wall is the wall of the protective pipe around the particle sensor which serves to protect the particle sensor and also to carry the exhaust gas and improve the deposition of particles on the electrodes. The device according to the invention improves the protection of the particle sensor from cracks due to high temperature differences at the ceramic components thereof as said temperature differences may occur as a result of water droplets adhering to or striking on the particle sensor after a water crossing operation.

BRIEF DESCRIPTION OF THE DRAWINGS

The invention is explained below in detail with the aid of an exemplary embodiment depicted in the figures. In the drawings.

DETAILED DESCRIPTION

Figure 1:
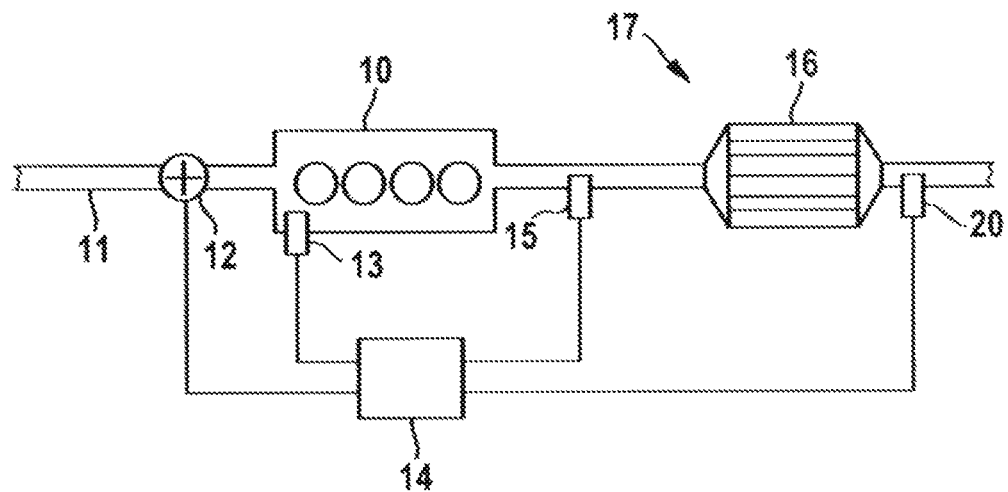
FIG. 1 shows, in a schematic depiction, the technical environment in which the method can be used.

FIG. 1 shows schematically the technical environment, in which the method according to the invention can be used. An internal combustion engine 10, which can be embodied as a diesel engine, is provided combustion air via an air inlet 11. In so doing, the air volume of the combustion air can be determined using an air flow meter 12 in the air inlet 11. The air volume can be used during a correction of a deposition probability of particles present in the exhaust gas of the internal combustion engine 10. The air volume being supplied furthermore serves to determine exhaust gas parameters, such as exhaust gas quantity, a volume flow or a speed. The exhaust gas of the internal combustion engine 10 is discharged via an exhaust gas tract 17 in which an exhaust gas emission control system 16 is disposed. Said exhaust gas emission control system 16 is embodied as a diesel particle filter. In addition, a lambda probe 15 and a particle sensor 20 are disposed in the exhaust gas tract 17, the signals of which are supplied to an engine management system 14. The engine management system 14 is furthermore connected to the air flow meter 12 and determines a fuel quantity on the basis of the data supplied thereto, which fuel quantity can be supplied via a fuel metering 13 of the internal combustion engine 10. In addition, the temperature of the particle sensor 20 that is required for carrying out the inventive method is determined in the engine management system 14, and release conditions for a regeneration of the particle sensor 20 or for the release of a measure phase of the particle sensor 20 are ascertained.

Figure 2:
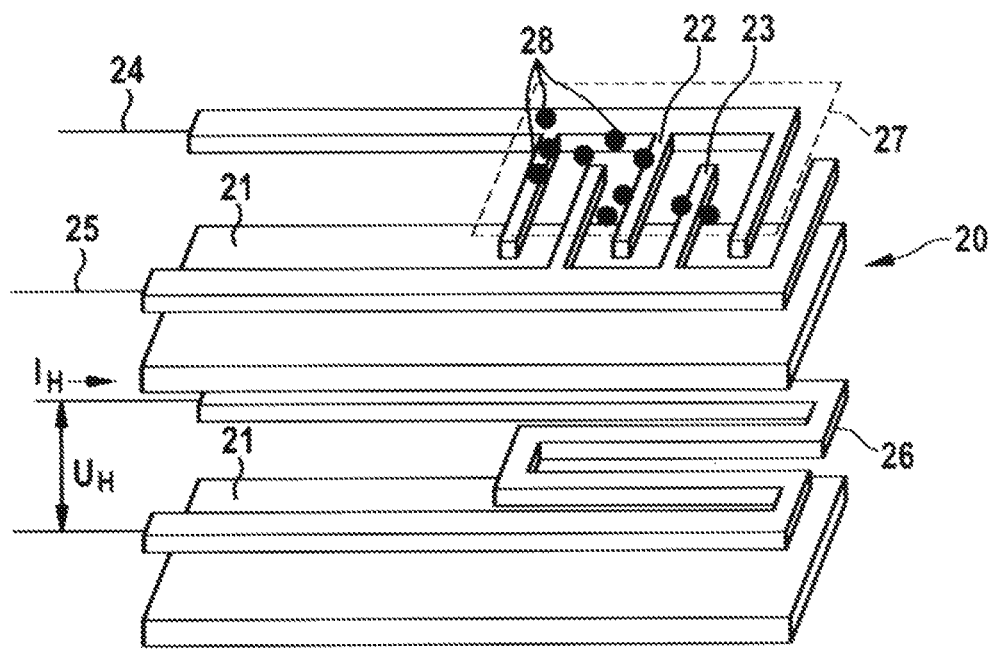
FIG. 2 shows an exhaust gas sensor embodied as a particle sensor.

FIG. 2 shows the particle sensor 20 in a schematic depiction. A first electrode 22 and a second electrode 23 are mounted to insulating substrates 21 which form a ceramic base body, for example consisting of aluminum oxide. The electrodes 22, 23 are embodied in the form of two mutually engaging comb electrodes (interdigital electrodes). A first terminal 24 and a second terminal 25 are provided on the end faces of the electrodes 22, 23. The electrodes 22, 23 are connected via said terminals to the engine management system 14 for the purpose of supplying voltage and for carrying out the measurement. In the exemplary embodiment, the electrodes 22, 23 and the uppermost insulating substrate 21, on which the electrodes 22, 23 are located, are covered with a protective layer 27. This optional protective layer 27 protects the electrodes 22, 23 from corrosion during the high operating temperatures of the particle sensor which prevail for the most part. In the example depicted, a heating element 26, which is connected via additional terminals to the engine management system 14 and can at least periodically be stressed by a heating voltage UH, is additionally integrated between the insulating substrates 21; thus enabling a heating current IH to flow. In order to measure the temperature, the heating element 26 itself can on the one hand be used or a temperature sensor element separately integrated into the particle sensor (e.g. as a meander-shaped Pt 100 resistance sheet or as a NTC or PTC ceramic sensor element).

If such a particle sensor is operated in a stream of gas carrying particles 28, for example in the exhaust gas tract 17 of an internal combustion engine 10, the particles 28 from the stream of gas are deposited on the particle sensor 20. In the case of a diesel engine, the particles 28 relate to soot particles.

In this connection, the deposition rate of the particles 28 on the particle sensor 20 is not only a function of the particle concentration in the exhaust gas but also inter alia of the voltage which is applied to the electrodes 22, 23. The loading with particles can, for example, be determined by means of a resistance or impedance measurement at the electrodes 22, 23 because the particles 28 are electrically conductive. If the particle sensor 20 is loaded with a layer of particles to the extent that particles 28 being additionally deposited do not lead to a further change in the resistance or the impedance of the particle sensor, the particle sensor 20 is then regenerated in a regeneration phase. To this end, the particle sensor 20 is heated with the aid of the heating element 26 to the extent that the deposited particles 28 are burned off.

Figure 3:
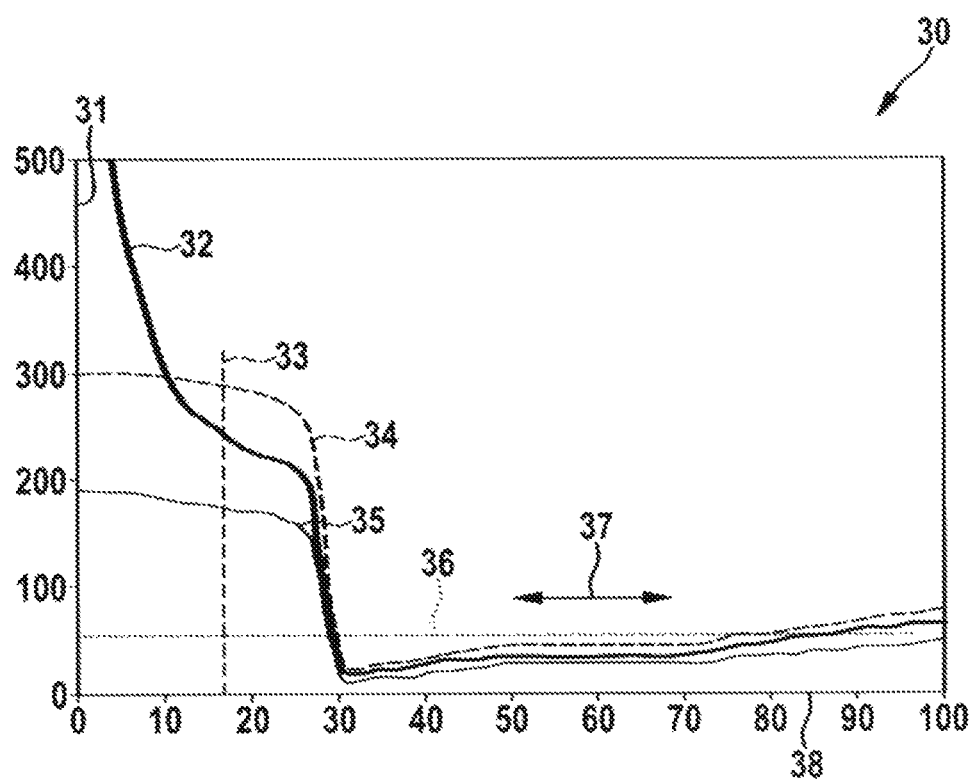
FIG. 3 shows a time diagram of temperature profiles in the exhaust gas duct during a water crossing.

In FIG. 3, temperature profiles in the exhaust gas tract 17 are shown in a time diagram 30 plotted over a time axis 38 and a signal axis 31. A temperature sensor on the particle sensor 20 emits a sensor temperature 32. In addition, the profile of an exhaust gas temperature 34 and a pipe wall temperature 35 are depicted. The pipe wall temperature 35 is the temperature of a protective pipe surrounding the particle sensor 20. At the beginning of the water crossing, the sensor temperature 32, the exhaust gas temperature 34 and the pipe wall temperature 35 drop sharply because water penetrates into the exhaust gas tract 17 and cools the components. After completion of the water crossing, the temperature signals rise again. In this respect, a temperature plateau typically emerges from this condition, wherein the water evaporates at a constant boiling temperature. The sensor temperature 32, the exhaust gas temperature 34 and the pipe wall temperature 35 subsequently continue to increase. After a detected water crossing state, a conclusion can be drawn about the current profile of the pipe wall temperature 35 and the exhaust gas temperature 34 by the analysis of the sensor temperature 32 when the heating element 26 is switched off. This is the case because the sensor temperature 32 lies between said two aforementioned temperatures 34, 35 in an application specific manner. It can be inferred from the termination of the temperature plateau 37 that the water has evaporated and the particle sensor 20 can be heated by means of the heating element 26 without risk of damage thereto. To this end, a release temperature 36 is predetermined, a release condition being generated in the engine management system 14 in the event of said release temperature being exceeded. This release condition can be logically linked to other signals, such as a release for regeneration or detection of the completion of a water crossing. All together it is therefore possible by means of the inventive method in contrast to the prior art to define the point in time at the installation position of the particle sensor 20, at which point in time the water is reduced to a sufficiently small amount after a water crossing operation so that a sensor regeneration or a sensor measurement phase can be released.

What is claimed is:

1. A method for regenerating a particle sensor (20), which comprises a ceramic base body, in an exhaust gas duct of an internal combustion engine (10) for driving a motor vehicle, comprising
   (a) determining a particle loading of the particle sensor (20),
   (b) determining a temperature of the particle sensor (20),
   (c) regenerating said particle sensor by heating with an electrical heating element (26),
   (d) after a water crossing operation of the motor vehicle with the heating element (26) switched off and the electrodes (22, 23) free of voltage, determining the temperature of the particle sensor (20), an exhaust gas temperature (34) and/or a pipe wall temperature (35) as a release condition that must be fulfilled before initiating regeneration of the particle sensor (20), and
   (e) considering the release condition fulfilled if the temperature determined in step (d) exceeds a predetermined release temperature (36).

2. The method according to claim 1, characterized in that the release condition is combined with a dew point release in order to release the particle sensor (20) or in that the release condition initiates a dew point release.

3. The method according to claim 1, characterized in that the release condition is combined with a release from a water crossing detection in order to release the particle sensor (20).

4. The method according to claim 1, characterized in that a profile of the temperature of the particle sensor (20), of the exhaust gas temperature (34) and/or of the pipe wall temperature (35) is collected after the water crossing operation and in that, after a temperature plateau (37) has been detected, the release condition is considered fulfilled if the predetermined release temperature (36) has been exceeded.

5. The method according to claim 1, characterized in that, the heating element (26) and the voltage at the electrodes (22, 23) are switched off after a water crossing state has been detected by an on-site control device of the particle sensor (20) and in that a switch-off signal is sent to a higher-level engine management system (14).

6. The method according to claim 1, wherein the particle loading of the particle sensor (20) is determined by applying an electrical voltage between at least two electrodes (22, 23) with interdigital arrangement, and wherein the temperature of the particle sensor (20) is determined with a temperature sensor mounted to the ceramic base body or from the electrical resistance of the heating element (26).

7. The method according to claim 6, wherein the temperature sensor is a meander.

8. The method according to claim 1, wherein after the water crossing operation of the motor vehicle, with the heating element (26) switched off and the electrodes (22, 23) free of voltage, the temperature of the particle sensor (20) is determined as the release condition that must be fulfilled before initiating regeneration of the particle sensor (20).

9. The method according to claim 1, wherein after the water crossing operation of the motor vehicle, with the heating element (26) switched off and the electrodes (22, 23) free of voltage, the exhaust gas temperature (34) is determined as the release condition that must be fulfilled before initiating regeneration of the particle sensor (20).

10. The method according to claim 1, wherein after the water crossing operation of the motor vehicle, with the heating element (26) switched off and the electrodes (22, 23) free of voltage, the pipe wall temperature (35) is determined as the release condition that must be fulfilled before initiating regeneration of the particle sensor (20).

11. The method according to claim 1, wherein after the water crossing operation of the motor vehicle, with the heating element (26) switched off and the electrodes (22, 23) free of voltage, the temperature of the particle sensor (20), the exhaust gas temperature (34), and the pipe wall temperature (35) are determined as the release condition that must be fulfilled before initiating regeneration of the particle sensor (20).

12. A device for regenerating a particle sensor (20), which comprises a ceramic base body, in the exhaust gas duct of an internal combustion engine (10), wherein the particle sensor (20) comprises at least two electrodes with interdigital arrangement for determining a particle load, a temperature sensor mounted to the ceramic base body for determining a sensor temperature (32) of the particle sensor (20) and an electrical heating element (26) for regenerating said particle sensor; and wherein an engine management system (14) is provided which controls the internal combustion engine and acquires and evaluates output signals of the particle sensor (20), characterized in that a circuit or a program sequence for detecting a water crossing operation and for evaluating the sensor temperature (32), an exhaust gas temperature (34) and/or a pipe wall temperature (35) is provided in the engine management system (14); and in that, after a water crossing operation, a release condition, that must be fulfilled before initiating regeneration of the particle sensor (20), is fulfilled if the sensor temperature (32), the exhaust gas temperature (34) and/or the pipe wall temperature (35) exceed a predetermined release temperature (36).

13. The device according to claim 12, wherein the temperature sensor is a meander.

14. The device according to claim 12, wherein the circuit or the program sequence is for detecting the water crossing operation and for evaluating the sensor temperature (32), and wherein the release condition is fulfilled if the sensor temperature (32) exceeds a predetermined release temperature (36).

15. The device according to claim 12, wherein the circuit or the program sequence is for detecting the water crossing operation and for evaluating the exhaust gas temperature (34), and wherein the release condition is fulfilled if the exhaust gas temperature (34) exceeds a predetermined release temperature (36).

16. The device according to claim 12, wherein the circuit or the program sequence is for detecting the water crossing operation and for evaluating the pipe wall temperature (35), and wherein the release condition is fulfilled if the pipe wall temperature (35) exceeds a predetermined release temperature (36).

17. The device according to claim 12, wherein the circuit or the program sequence is for detecting the water crossing operation and for evaluating the sensor temperature (32), the exhaust gas temperature (34), and the pipe wall temperature (35), and wherein the release condition is fulfilled if the sensor temperature (32), the exhaust gas temperature (34), and the pipe wall temperature (35) exceed a predetermined release temperature (36).

18. A method for regenerating a particle sensor (20), which comprises a ceramic base body, in an exhaust gas duct of an internal combustion engine (10) for driving a motor vehicle, comprising (a) determining a particle loading of the particle sensor (20),
(b) determining a temperature of the particle sensor (20),
(c) regenerating said particle sensor by heating with an electrical heating element (26),
(d) after a water crossing operation of the motor vehicle with the heating element (26) switched off and the electrodes (22, 23) free of voltage, determining the temperature of the particle sensor (20), an exhaust gas temperature (34) and/or a pipe wall temperature (35) as a release condition that must be fulfilled before initiating a measurement phase during which the particle loading of the particle sensor (20) is determined, and
(e) considering the release condition fulfilled if the temperature determined in step (d) exceeds a predetermined release temperature (36).

19. The method according to claim 18, wherein after the water crossing operation of the motor vehicle, with the heating element (26) switched off and the electrodes (22, 23) free of voltage, the temperature of the particle sensor (20) is determined as the release condition that must be fulfilled before initiating a measurement phase during which the particle loading of the particle sensor (20) is determined.

20. The method according to claim 18, wherein after the water crossing operation of the motor vehicle, with the heating element (26) switched off and the electrodes (22, 23) free of voltage, the exhaust gas temperature (34) is determined as the release condition that must be fulfilled before initiating a measurement phase during which the particle loading of the particle sensor (20) is determined.

21. The method according to claim 18, wherein after the water crossing operation of the motor vehicle, with the heating element (26) switched off and the electrodes (22, 23) free of voltage, the pipe wall temperature (35) is determined as the release condition that must be fulfilled before initiating a measurement phase during which the particle loading of the particle sensor (20) is determined.

22. The method according to claim 18, wherein after the water crossing operation of the motor vehicle, with the heating element (26) switched off and the electrodes (22, 23) free of voltage, the temperature of the particle sensor (20), the exhaust gas temperature (34), and the pipe wall temperature (35) are determined as the release condition that must be fulfilled before initiating a measurement phase during which the particle loading of the particle sensor (20) is determined.

* * * * *